United States Patent [19]

Kilbride, Jr.

[11] Patent Number: 4,994,458
[45] Date of Patent: Feb. 19, 1991

[54] PROCESS FOR ROTARY FLUID BED GRANULATION OF RIBOFLAVIN

[75] Inventor: Terence K. Kilbride, Jr., Bloomfield Hills, Mich.

[73] Assignee: BASF Corporation, Parsippany, N.J.

[21] Appl. No.: 516,398

[22] Filed: Apr. 30, 1990

[51] Int. Cl.$^5$ .................. A61K 31/525; A61K 9/16
[52] U.S. Cl. .................. 514/251; 424/489; 264/109; 264/114; 264/117
[58] Field of Search .............. 514/251; 424/489; 264/109, 114, 117

[56] References Cited

U.S. PATENT DOCUMENTS

| | | | |
|---|---|---|---|
| 3,959,472 | 5/1976 | Cawnalonga et al. | 514/251 |
| 4,486,435 | 12/1984 | Schmidt et al. | 514/251 |
| 4,540,602 | 9/1985 | Motoyama et al. | 424/494 |
| 4,563,315 | 1/1986 | Walter | 264/114 |
| 4,643,898 | 2/1987 | Peters et al. | 514/251 |
| 4,721,716 | 1/1988 | Neesby | 514/251 |
| 4,725,427 | 2/1988 | Ashmead et al. | 514/251 |
| 4,840,799 | 6/1989 | Appelgren et al. | 424/490 |
| 4,868,180 | 9/1989 | Izuhara et al. | 514/251 |

FOREIGN PATENT DOCUMENTS

| | | |
|---|---|---|
| 216653 | 4/1987 | European Pat. Off. . |
| 345717 | 12/1989 | European Pat. Off. . |
| 2341504 | 3/1975 | Fed. Rep. of Germany . |
| 2551578 | 5/1977 | Fed. Rep. of Germany . |
| 3819745 | 12/1989 | Fed. Rep. of Germany . |

OTHER PUBLICATIONS

Jager et al., Pharm. Ind., 44(2):193–196 (1982), Effect of Material Motion on Agglomeration in the Rotary Fluidized-Bed Granulator.

Olsen, Plant/Operations Progress, 4(3):135–138, Jul. 1985, "Recent Advances in Fluid Bed Agglomeration and Coating Technology".

*Primary Examiner*—Shep K. Rose
*Attorney, Agent, or Firm*—Rupert B. Hurley; Michael R. Chipaloski

[57] ABSTRACT

A riboflavin granulate containing from 75 to 99.5 weight percent riboflavin is produced by:

A. placing a desired quantity of riboflavin powder in the bowl of a rotary fluid bed granulator;
B. fluidizing the powder with fluidizing air while rotating the rotor disc, whereby a fluidized cloud of riboflavin powder is produced; and
C. spraying a binder solution into the fluidized cloud;

so that at least 90 weight percent of the riboflavin powder combines to form granules.

20 Claims, No Drawings

4,994,458

PROCESS FOR ROTARY FLUID BED GRANULATION OF RIBOFLAVIN

BACKGROUND OF THE INVENTION

The present invention pertains to granulation processes, more specifically to a process for forming a granulate which comprises between about 75 weight percent and about 99 weight percent of riboflavin and between about 1 weight percent and about 25 weight percent of a binder. Moreover, the present invention pertains to a method of making a riboflavin-containing granulate via rotary fluid bed granulation.

Riboflavin is available as a fine powder of various purities (90 to 100 percent) comprised of riboflavin crystals 0.5 to 2 microns wide and 1 to 25 microns long. This powder is clingy, dusty and electrostatic. The powder sticks to and fouls processing equipment with which it comes into contact. Furthermore, the powder tends to bridge and clump during handling. There can be significant losses due to a buildup of riboflavin powder on the processing equipment utilized in the food and feed, and pharmaceutical industries. In addition, substantial labor must be expended to remove adhering riboflavin powder from the equipment.

In the feed industry, riboflavin powder can be made more manageable (i.e., non-dusty, non-adherent, and free-flowing), by spray drying an aqueous slurry of approximately 25% weight percent riboflavin, approximately 25% weight percent filler, and about 50% water. The filler is generally any water-soluble starch, corn syrup, dextrin, or pregelatinized starch. The filler improves the performance of the powder by encapsulating the riboflavin. However, this method is not suitable for the food and pharmaceutical industries because the pharmaceutical and food industries require high riboflavin concentrations, i.e., riboflavin concentrations of between 90 percent by weight and 100 percent by weight.

Prior to this invention, in the pharmaceutical and food industries, concentrated riboflavin powders (i.e., 90 to 100 weight percent) have been used in powder form. However, as noted above, this powder presents flowability, handling, and processing problems. The method of the present invention enables the production of a 90 to 100 weight percent riboflavin product which has heretofore unachieved flowability characteristics.

Related art of which the inventors are aware is: U.S. Pat. No. 4,868,180 (as well as the European counterpart application 0,219,276): K. W. Olsen, "Recent Advances in Fluid Bed Agglomeration and Coating Technology", Plant/Operations Progress, Vol. 4, No. 3, pp. 135–138, July 1985; U.S. Pat. No. 3,962,384; and U.S. Pat. No. 4,486,435. None of this art discloses the use of a rotary fluid bed device for the granulation of riboflavin.

The '384 and '435 patents are directed at compositions which have a binder present in an amount around 50 weight percent. The use of large amounts of binder (i.e., amounts greater than 25 weight percent, based on total dry product weight) enables the complete granulation of the vitamin B particles, whereas complete granulation (i.e., less than 10 weight percent ungranulated vitamin crystals) is much more difficult to achieve if less than 25 weight percent binder is utilized.

The Olsen article describes the operation of a rotary granulator/coater, but the Olsen article nowhere mentions the use of such a device for the granulation of a riboflavin product. When using conventional fluid bed and spray drying operations, it has been found that if the mixture being granulated contains a proportionally large amount of riboflavin (i.e., 50 weight percent, or more), material adheres to the surfaces of the equipment, producing low product yields, and requiring significant effort to remove the adhering material from the equipment, unless special and unusual care is taken to minimize the adherence of riboflavin by mechanical mixing or exceptionally long cycle times (which renders the process cumbersome and uneconomical). The inventor of the present invention has surprisingly found that a rotary fluid bed granulator can granulate a riboflavin product comprising at least 75 weight percent riboflavin while obtaining very high yields, and without having significant amounts of material adhering to the surfaces of the equipment. Furthermore, it has surprisingly been found that the granulation is substantially complete (i.e., very few ungranulated riboflavin crystals remain in the product produced) within an economical cycle time. In contrast, the Olsen article nowhere refers to vitamin products, not to mention riboflavin products comprising riboflavin in an amount of at least 75 weight percent.

U.S. Pat. No. 4,868,180 describes a 90–99% vitamin B granulate which is made by conventional fluid bed granulation, followed by pulverizing the resulting granulate in a Fitz mill. The '180 powder nowhere refers to rotary fluid bed granulation. The '180 patent nowhere refers to the product yield. The '180 patent nowhere states that the process produces a product which is completely granulated (i.e., at least 90 weight percent granulated). In contrast to the '180 patent, the inventors of the present invention have unexpectedly found that even if the amount of binder is 25 weight percent or less, at least 90 weight percent of the riboflavin powder can be granulated via rotary fluid bed granulation. In other words, the resulting level of ungranulated pure riboflavin is, at most, only 10%. Furthermore, the inventors have unexpectedly found that product yield is very high (generally from about 97 percent to about 99 percent, based on amount of riboflavin added) when a rotary fluid bed granulator is utilized. Furthermore, the process of the present invention does not require the use of any sort of degranulation or deagglomeration of large granules or agglomerates, unlike the process described in the '180 patent, which requires a Fitz milling step. It has been unexpectedly found that in the process of the present invention a substantially fully granulated 75-plus weight percent riboflavin product can be produced via rotary fluid bed granulation, with a product yield of at least 98 weight percent, without any "degranulation" or "deagglomeration" step (e.g., milling, screening, etc.).

BRIEF DESCRIPTION OF THE INVENTION

The present invention pertains to a batch process for the manufacture of a granulate which comprises riboflavin in an amount of at least 75 weight percent (on a dry weight basis), the process taking place in a rotary fluid bed granulator. The process comprises placing an aliquot of riboflavin powder into the product bowl of the roto-granulator unit, i.e., on the rotor disc therein. The amount of riboflavin powder added to the product bowl should be such that the resulting granulate product comprises riboflavin in an amount of from about 75 to about 99.5 weight percent, dry basis. The riboflavin powder is then fluidized by the centrifugal force of the rotating disc together with air which has been forced upwards between the outer periphery of the rotor disc and the inside wall of the roto-granulator unit. This produces a fluidized cloud of riboflavin powder. A binder solution is then sprayed onto the fluidized powder, the binder being added in an amount of from about 0.5 weight percent to about 25 weight percent, based on the weight of the resulting granulate, dry basis. The above process steps are carried out so that at least 90 weight percent of the riboflavin powder combines with the binder to form granules. The resulting product comprises from about 75 weight percent riboflavin to about 99.5 weight percent riboflavin, and from about 0.5 weight percent binder to about 25 weight percent binder.

It is an object of the present invention to enable the production of a granulated 75-plus weight percent riboflavin product which has a high flowability.

It is a further object of the invention to enable the production of a riboflavin product without the adherence of riboflavin powder to equipment during the production process.

It is a further object of the invention to enable the production of a 90 to 99.5 weight percent riboflavin product which is suitable for incorporation into food and/or pharmaceutical end uses.

It is a further object of the present invention to enable the production of a riboflavin product which can be uniformly mixed into other food and/or pharmaceutical ingredients.

It is a further object of the present invention to produce a granulated riboflavin product with a process having a yield of at least 90 weight percent granulate.

It is a further object of the present invention to produce a granulated riboflavin product via a rotary granulation process.

It is a further object of the present invention to provide a process for making a granulate which is both high in riboflavin content and which has excellent flowability characteristics.

It is a further object of the present invention to produce a riboflavin granulate via a batch granulation process.

DETAILED DESCRIPTION OF THE PREFERRED EMBODIMENTS

In addition to granules and agglomerates, the phrase "ungranulated pure riboflavin" is also utilized herein. This phrase refers to that portion of the riboflavin which is not bound to the binder utilized in the formulation. Ungranulated pure riboflavin contains individual riboflavin crystals in the form of particles which are much smaller than the specified granule size. Ungranulated pure riboflavin is, in general, comprised of either individual riboflavin crystals or agglomerates of riboflavin crystals of which may range in size from very small to (e.g. a fraction of a micron) to very large (e.g. 20 millimeters). As used herein, the phrase "ungranulated pure riboflavin" refers to all individual riboflavin crystals or agglomerates of crystals which are not bound to the binder material.

The process of the present invention pertains to a process for making a riboflavin granulate, in which the granulate (in general) is comprised of riboflavin in an amount of from about 75 weight percent to about 99.5 weight percent, on a dry basis. However, the granulate preferably comprises riboflavin in an amount of from about 90 weight percent to about 99.5 weight percent, and most preferably comprises riboflavin in an amount of from about 94 weight percent to about 96 weight percent. More importantly, the process of the present invention produces a granulate via rotary fluid bed granulation (also known as a roto-granulation). It has been unexpectedly found that, unlike processes utilizing a spray dryer or an ordinary fluid bed, the use of a rotary fluid bed granulator does not result in the significant buildup of this difficult-to-handle powder on the internal surfaces of the rotary granulator. Rather, it has surprisingly been found that there is a relatively small amount of buildup of material on the internal surfaces of the rotary granulator. A yield of from about 97 weight percent to about 99 weight percent has been achieved with the process of the present invention, based on the weight of the starting materials. The only buildup of material found to occur has been on the rotor disc itself, this buildup amounting to less than about 3 weight percent, based on the weight of the starting materials. In stark contrast, conventional fluid bed processes typically have resulted in a yield of granulated riboflavin of only about 50 weight percent, based on the weight of the starting materials, due to a buildup of material on the inside surfaces of the granulating equipment.

In the operation of the rotary granulator, there is a vertical upward flow of air around the periphery of the rotor disc. It has been found that this airflow has the effect of keeping the inside wall of the product bowl free of buildup of the riboflavin powder. This airflow also has the effect of fluidizing the riboflavin powder by lifting the powder upward from the surface of the rotor disc. For any given rotor disc, the "air-speed" (i.e., the linear rate of travel of the air rising up around the perimeter of the rotor disc) is determined by two variables: (1) the total area making up the gap between the interior surface of the product bowl and the outermost edge of the rotor disc, and (2) the amount of air which flows through the gap per unit time (i.e., cubic meters per minute). The airspeed is proportional to the fluidizing force of the air.

In general, the gap between the product bowl and the rotor disc (i.e., the slit width) is from about 1 millimeter to about 10 millimeters. Preferably the gap is from about 1 millimeter to about 5 millimeters. Most preferably the gap is about 2.5 millimeters. In general, roto-granulation units range in capacity from about a 3 kg charge to about a 350 kg charge with roto disc diameters of from about 0.3 meters to about 1.4 meters respectively. In general, the air velocity through the gap (i.e. slit) between the rotor and the product bowl is from about 200 meters per minute to about 8000 meters per minute. Preferably the air flow through the gap is from about 1000 meters per minute to about 8000 meters per minute. Most preferably the airflow through the gap is about 6000 meters per minute. In general, the rotor disc should rotate at a circumferential speed of from about 3 meters per second to about 25 meters per second. Preferably, the rotor disc should rotate at a speed of from about 3 meters per second to about 13 meters per second. Most preferably, the rotor disc should rotate at a speed of about 7.5 meters per second. The rotation of the disc produces a centrifugal force which causes the riboflavin powder to move radially outward, toward the outermost edge of the rotating rotor disc. This movement, of course, causes the riboflavin powder to come into contact with the fluidizing air which is rising vertically from around the peripheral edge of the rotor disc. Once the powder reaches the edge of the rotor disc, the powder is fluidized by being forced upward. A fluidized cloud of powder results. Upon approaching a peak height (which height is dependent upon the airspeed, the density of the powder particles, etc.), the powder particles tend to move radially inward, with the airflow, because this "inner" volume has a slightly lower pressure than the "outer" volume. Thus, a helical flow path is produced within the rotary granulator.

The fluidized powder is granulated by spraying a binder solution thereon during the fluidization process. The spraying is preferably carried out via spray-atomizing the binder solution into the fluidized cloud of riboflavin. The atomized spray of binder solution is preferably sprayed directly into the fluidized cloud of riboflavin powder. The rate of addition of binder affects the size of the granules produced. Other variables which control the size of the granules produced include the rate of rotation of the disc, the fluidizing air flow rate (i.e., cubic meters of air per minute flowing through the gap), and the gap width. In general, the rate of addition of the binder solution can be from about 1 gram of binder solution per minute per kilogram of riboflavin within the roto-granulator to about 40 grams per minute per kilogram riboflavin. Preferably, the rate of addition of the binder solution is from about 20 grams per minute per kilogram to about 40 grams per minute per kilogram. Most preferably, the binder solution is added at a rate of about 170 grams per minute per kilogram. The higher the rate of addition of the binder solution, the greater the particle size. For example, if the binder solution is added at a rate of about 36 grams binder solution per minute per kilogram riboflavin, the resulting mean granule diameter was about 469 microns, whereas when the binder solution was added at a rate of about 165 grams per minute per kilogram, the resulting mean granule diameter was about 254 microns.

As stated above, the binder is preferably spray-atomized into the fluidized cloud of riboflavin powder. Preferably a two-phase binder addition nozzle is used to spray-atomize the binder solution into the fluidized cloud of riboflavin powder. The binder is preferably pumped out through a central orifice, whereas the atomizing fluid (preferably air) is forced out through the outer orifice. Preferably the atomizing air is forced through the outer orifice under high pressure, i.e., generally at a pressure of between about 1 bar and about 5 bar, most preferably about 3 bar.

A binder is also utilized in the process of the present invention. The binding agent is a water-soluble binder or a binder soluble in an organic solvent. The water-soluble binder may be a pregelatinized starch, water-soluble cellulose, a water-soluble high polymer, etc. A pregelatinized starch is a starch prepared by heating a dispersion of starch in water or a dry starch obtained by drying the same. The pregelatinized starch is exemplified by pregelatinized corn starches, pregelatinized potato starches, and pregelatinized modified starches [e.g., those described in Code of Federal Regulations (U.S.A.) §121, 1031a, b, c, d, e, f, g, and h]. Furthermore there are pregelatinized dry commercial products such as Amycol C (Nichiden Chemical Company, Japan), Amylox (Nihon Corn Starch Company, Japan), Pre-Gel (Hublinger Company, U.S.A.), or Instant Cleargel (National Starch Company, U.S.A.).

Examples of water soluble celluloses include, for example, hydroxypropylcellulose, hydroxymethylcellulose, hydroxypropylmethylcellulose, carboxymethylcellulose, methylcellulose, etc. The water-soluble high molecular weight compounds (water-soluble high polymers) are exemplified by polyvinylpyrrolidone, polyvinyl alcohol, dextrin, gum arabic, gelatin, polydextrose, etc.

Binding agents soluble in organic solvents may be, for example, cellulose derivatives soluble in organic solvents, such as cellulose acetate phthalate, hydroxypropylmethylcellulose phtalate, ethylcellulose, etc. However, water-soluble binders (especially water-soluble celluloses) are preferred over binding agents soluble in organic solvents.

The solvent used to prepare a solution containing a binding agent or spraying includes water and organic solvents, for example lower alcohols (e.g., methylalcohol, ethylalcohol, isopropylalcohol, etc.) as well as ketones (e.g., acetone, etc.).

It is preferred that the binder utilized in the process is at least one member selected from the group consisting of water-soluble celluloses: hydroxypropylmethylcellulose, hydroxypropylcellulose, hydroxymethylcellulose, carboxymethylcellulose, and methylcellulose. It is most preferred that the binder is hydroxypropylmethylcellulose.

Not only is the rate of binder addition important in the process, so too is the total amount of binders added in the process. The total amount of binders added in the process may be from about 0.5 weight percent of the product to about 25 weight percent of the product, dry product basis. Preferably the amount of binder in the product is from about 0.5 to about 10 weight percent of the product, and most preferably the amount of binder in the product is from about 3 to about 5 weight percent of the product. In general, it is preferred to have as little binder as is necessary while producing coherent granules with very little or no ungranulated pure riboflavin powder present in the product.

As stated above, the binder is sprayed into the rotary granulator in the form of a binder solution. The solution is comprised of one or more of the above binders dissolved in a solvent therefor. In general, the solvent is at least one member selected from the group consisting of water and organic solvents, for example lower alcohols (e.g., methylalcohol, ethylalcohol, isopropylalcohol, etc.) as well as ketones (e.g., acetone, etc.). Preferably, the solvent is at least one member selected from the group consisting of water and organic solvents. Most preferably the solvent is water. The concentration of the binder in the solvent is, in general, from about 2 weight percent to about 10 weight percent, based on the total weight of the binder solution. Preferably the concentration of binder in the solvent is from about 4 weight percent to about 8 weight percent. Most preferably the concentration of binder in the solvent is about 8 weight percent.

In order to effectuate the formation of granules, it is necessary to carry out the granulation process at a temperature higher than room temperature. This elevated temperature is necessary in order to evaporate the solvent so that the binder will then cause the adhesion of powder particles to one another. The most desirable operating temperature is dependent upon the particular solvent being used in the process, but, in general, the temperature is from about 25° C. to about 100° C. Preferably the temperature is from about 25° C. to about 75° C. Preferably the temperature is around 60° C. Temperatures above ambient have been achieved by passing the fluidized air through a steam heat exchanger.

It is also desirable to heat the binder solution so that the binder solution enters the rotary granulator at a temperature above ambient temperature. The elevation of the binder temperature enables the rapid dissolution of the binder in the solvent during preparation of the binder solution before spray drying. In general, the temperature of the binder solution (for the preferred binder, hydroxypropylmethylcellulose) should be from about 20° C. to about 60° C. Preferably, the binder temperature is from about 35° C. to about 45° C., and most preferably the binder temperature is about 40° C.

As stated above, the process of the present invention is, in general, a batch process, although it is conceivable that a continuous process could be developed. In general, the length of time required to granulate a batch of riboflavin of powder is from about 10 minutes to about 60 minutes. Preferably the batch time is from about 15 minutes to about 30 minutes. Most preferably the batch time is about 22 minutes.

FLODEX METHOD FOR FLOWABILITY DETERMINATION

Flowability was measured using a Flodex ® Powder Flowability Index Test Instrument, Model 211, purchased from Hanson Research Corporation, 19727 Bahama Street, P.O. Box 35, Northridge, Calif., 91328. The Flodex ® apparatus presents a sample method for repeatable determination of powder flow characteristics. The Flodex ® device operates based upon the ability of a powder to fall freely through a hole in a plate. As used herein the Flowability Index was calculated by dividing 1000 of the orifice diameter in millimeters. For example, powder which will pass through an orifice diameter 4 millimeters in diameter, but not smaller, has a Flowability Index of 250.

The setup and operation of the Flodex ® Powder Flowability Index Test Instrument is thoroughly described in the Instruction Manual for the Flodex ® Model 211 apparatus, this Instruction Manual being hereby incorporated by reference. In addition, below is briefly described the method of determining flowability when using this device.

First a 50 gram sample of the powder to be tested was used to fill the receptacle cylinder (funnel) to within about a centimeter from the top of the cylinder. The powder was carefully loaded onto the funnel so that there was no packing of the powder within the funnel (of course, packing would have caused a loss of flowability of the powder). After the loading of the funnel, a minimum of 30 seconds was allowed to pass before the test was begun, in order to allow the possible formation of any flocculi. To begin the test, the release lever was slowly moved forward to drop open the hold closure, without vibration. If the test was positive, the open hole was visible from the top when looking down to see the hole at the bottom. The Flodex ® device should not be tapped or shaken during the test. If the test results were positive, the test was repeated with a smaller orifice diameter, until the orifice was of such a small diameter that a negative result (i.e., lack of flow) was achieved.

The Flodex ® apparatus is supplied with nineteen disks, from 4 to 32 millimeter hole diameters in one millimeter increments from 4 to 10 millimeters and in 2 millimeter increments for disks having a hole greater than 10 millimeters in diameter. In addition to these disks, the inventors herein had 2 additional disks fabricated, one with a 2 millimeter hole, the other with a one millimeter hole. These two additional disks provided a means for determining flowability indexes of 500 to 1000, respectively.

In general, the granulated riboflavin product of the present invention should have a Flodex (i.e., flowability index) of from about 75 to about 750, and preferably the Flodex is from about 100 to about 500. Most preferably, the Flodex is from about 150 to about 350.

EXAMPLE 1

This example illustrates a procedure for the preparation of a free-flowing, roto-granulated, static-free riboflavin powder which contained over 95% by weight riboflavin in the resulting granulate.

A binder solution was formulated in a five-gallon tank containing 92 parts of water, heated to 40° C. by a hot plate. 8 Parts of water-soluble hydroxypropylmethylcellulose, sold under the trademark "Methocel E-5", were dissolved into the hot water by stirring. This mixture was stirred for approximately 0.5 hours to completely dissolve the Methocel E-5.

3 Kilograms of a commercially available riboflavin powder having a purity of 99% to 100% were charged into the bowl of a laboratory size roto-granulator, having a variable speed rotating disk (which had a diameter of about 480 millimeters), feed tanks, and binder solution pump. The riboflavin was fluidized by two distinct forces: the rotating disk, turning at 200 rpm, and fluidizing air, with between 200 and 300 cubic feet per minute passed through the slit (a gap of about 2 millimeters) between the rotating disk and the inner wall of the bowl of fluid bed. After the riboflavin was fluidized, the previously prepared binder solution was sprayed tangentially (at a rate of 165 grams per minute) into the riboflavin cloud through a two-fluid 1.2 mm nozzle utilizing 3.0 bar air to atomize the binder solution. After the binder solution was complete, the granulated riboflavin powder was dried by raising the inlet temperature of the fluidizing air to 72° C.

The resulting riboflavin powder was an orange, free-flowing, static-free powder having a bulk density of 0.38 grams per cubic centimeter and a geometric mean particle size of about 250 microns with a log standard deviation of about 1.9 microns. The flowability index, as measured by the Flodex method, was found to be about 200. [Any value greater than or equal to 100 is indicative of excellent flowability.] The resulting granulate was directly compressed to form tablets. The product was made up of about 96 weight percent riboflavin, 3.75 percent binder, and 0.25 weight percent water. The tablets had a hardness of 15.5 scu.

EXAMPLE 2

This example illustrates that an ordinary fluid bed (i.e. a fluid bed which does not utilize a rotary tray) was not suitable for granulating riboflavin because a fluid bed did not completely fluidize the riboflavin crystals. This phenomenon prevented the production of a homogeneous granulated product in a fluid bed.

While 95 parts of riboflavin crystals and 1 part silica, Aerosil 200, a fluidizing aid, were being fluidized in a fluidized bed granulator (a Glatt CPCG 5-UD manufactured by Glatt AG of West Germany, using dry air heated up to 60° C.), an 8 weight percent aqueous solution of hydroxypropylmethylcellulose was sprayed onto the fluidized powders up to the amount equivalent to 4 parts on a dry basis. The spraying of the binder solution was conducted over an 8.5 minute time period.

Fluidization continued for an additional 28 minutes to completely dry the powder.

The product had the following particle size distribution:

| Sieve Designation A.S.T.M. -E-11-61 | Sieve Opening Microns | Weight % Retained On |
|---|---|---|
| 6 | 3,360 | 13 |
| 20 | 841 | 35 |
| 40 | 420 | 31 |
| 60 | 250 | 16 |
| 100 | 149 | 4 |
| 120 | 125 | 1 |
| Pan | — | 0 |

The bulk density of the resulting product was 0.30 grams per cubic centimeter and the powder contained 0.25 weight percent water. The particles larger than 841 microns were spherical and possessed no mechanical strength. Upon handling they would break apart into a fine yellow powder. This powder was ungranulated riboflavin crystals (i.e., agglomerated riboflavin), and the large balls were formed by electrostatic forces generated by fluidizing the ungranulated riboflavin crystals during the drying step. In contrast, the remaining powder (i.e. that fraction which passed through a 20 mesh sieve), consisted of orange granulated particles and possessed a flowability index (as measured by the Flodex method) of 71. The product produced in the fluid bed was not suitable for tableting. The large spherical balls significantly reduced the flowability. This prevented an even distribution and steady flow of riboflavin through the die of the tablet press. However, of the granulated particles, those particles which passed through a 20 mesh sieve were suitable for tabletting, and produced directly compressible tablets with a hardness of 25 scu.

The lack of mechanical strength of the large spherical particles, i.e., particles larger than 841 microns, combined with the exceptionally hard tablets produced from the granulated material, i.e., particles smaller than 841 microns, indicated that the product was not homogenous, i.e., that approximately 50% of the powder was ungranulated riboflavin crystals while the other 50% was granulated. However, because the amount of binder sprayed into the fluidized riboflavin was designed to produce a granulate containing 95 weight percent riboflavin, on a dry basis, and 50% of the powder was not granulated, the assay of the granulated material was much lower than was desired. Analytical analysis confirmed that the particles greater than 841 microns were ungranulated and that they possessed an assay of 100% riboflavin, while the granulated particles had an assay of 89.1% riboflavin.

In spite of the fact that the above-described Example did not result in the production of a riboflavin granulate having a flowability of from 75 to 750, the inventor is aware that certain fluid bed processes can in fact, occasionally produce such a granulate. However, in order to produce such a riboflavin granulate with a fluid bed, the inventors have discovered that (1) the rate of addition of binder solution must be lower than is commercially desired; (2) the process is only operable on larger-than-lab-scale fluid beds; (3) chopper blades may be required; (4) drying times are longer than commercially desired.

EXAMPLE 3

This example illustrates that Fitz milling the powder produced in a fluid bed granulator (which was done in example 7 of the U.S. Pat. No. 4,868,180) does not improve the flowability or suitability for use in direct compressible tablets or food blends.

While 95 parts of riboflavin crystals were fluidized in a fluidized bed granulator using dry air heated to 50° C., a 5 weight percent aqueous solution containing hydroxypropyl methylcellulose was sprayed onto the fluidized powders up to an amount equivalent to 3 parts on a dry basis. Fluidization continued for an additional 15 minutes to completely dry the powder. The powder was pulverized in a Fitz mill using a punched screen with openings 1.5 mm in diameter. The resulting powder was dusty, static prone, and exhibited flow only in large clumps. The powder had a flowability index of 33, by the Flodex method, and a bulk density of 0.26 grams per cubic centimeter. The powder was not considered suitable for use in directly compressible tablets or food blends, where reasonable flowability was required for processing.

I claim:

1. A process for making a riboflavin granulate, the process comprising the steps of:
    A. placing riboflavin powder into a product bowl of a rotary fluid bed granulator, wherein the amount of riboflavin added to the product bowl is calculated to produce a granulated product comprising riboflavin in an amount from about 75 to about 99.5 weight percent, dry basis;
    B. fluidizing the powder with fluidizing air which has been forced upward around the periphery of a rotor disc within the granulator, while simultaneously rotating the rotor disc, whereby a fluidized cloud of the riboflavin powder is produced, and
    C. spraying a binder solution into the fluidized cloud of riboflavin powder, the binder being added in an amount of from about 0.5 weight percent to about 25 weight percent, based on the weight of the resulting granulate, dry basis;

so that at least 90 weight percent of the riboflavin powder combines with the binder to form granules.

2. A process as described in claim 1, wherein a gap between the product bowl and the rotor disc is from about 1 millimeter to about 10 millimeters.

3. A process as described in claim 2, wherein the gap is from about 1 millimeter to about 5 millimeters.

4. A process as described in claim 1 wherein the granulation process is carried out at a temperature of from about 25° C. to about 100° C. within the rotary fluid bed granulator.

5. A process as described in claim 1 wherein the granulation process is carried out at a temperature of from about 25° C. to about 75° C. within the rotary fluid bed granulator.

6. A process as described in claim 1 wherein a binder is spray-atomized within the rotary fluid bed granulator during the granulation process, and wherein the binder is sprayed into the granulator at a rate of about 1 gram binder solution per minute per kilogram riboflavin present to about 40 grams per minute per kilogram.

7. A method as described in claim 6 wherein the binder is spray-atomized within the granulator at a rate of from about 20 grams per minute per kilogram to about 40 grams per minute per kilogram.

8. A method as described in claim 6 wherein the binder is spray-atomized within the granulator at a rate of about 34 grams per minute per kilogram during the granulation process.

9. A process as described in claim 1, wherein the granulation process is a batch process and the granulation process is carried out over a time period of from about 10 minutes to about 60 minutes.

10. A process as described in claim 1 wherein the resulting riboflavin granulate is comprised of from about 90 weight percent riboflavin to about 99.5 weight percent riboflavin.

11. A process as described in claim 1 wherein the yield of the process is from about 97 weight percent to about 99 weight percent, and wherein less than about 3 weight percent of the riboflavin adheres to an internal surface within the granulator.

12. A process as described in claim 1 wherein the binder is a water-soluble binder, and wherein the binder is at least one member selected from the group consisting of pregelatinized starches, water-soluble celluloses, and water-soluble high polymers.

13. A process as described in claim 12 wherein the binder is at least one member selected from the group consisting of pregelatinized corn starches, pregelatinized potato starches, pregelatinized modified starches, hydroxypropylcellulose, hydroxymethylcellulose, hydroxypropylmethylcellulose, carboxymethylcellulose, methylcellulose, polyvinylpyrrolidone, polyvinylalcohol, dextrin, gum arabic, gelatin and polydextrose.

14. A method as described in claim 1 wherein the binder is spray-atomized into the rotary fluid bed granulator via a two-phase binder addition nozzle.

15. A process as described in claim 1, wherein the rotary fluid bed granulator has a rotor disc therein, the rotor disc is rotated at a circumferential speed of about 3 m/sec to about 25 m/sec.

16. A process as described in claim 1 wherein the rotor disc is rotated at a rate of from about 3 m/sec to about 13 m/sec.

17. A process as described in claim 1, wherein the rotor disc is rotated at a rate of about 7.5 m/sec.

18. A process as described in claim 2, wherein the fluidizing air traveling through the gap has a velocity of from about 200 m/min to about 8000 m/min.

19. A process as described in claim 3 wherein the fluidizing air traveling through the gap has a velocity of from about 1000 m/min to about 8000 m/min.

20. A process as described in claim 1, wherein the amount of riboflavin added is calculated to produce a granulated product comprising riboflavin in an amount of from about 94 weight percent to about 96 weight percent, dry basis, and wherein the rotor disc is rotating at a circumferential speed of about 7.5 meters per second, and wherein the temperature within the rotogranulator is about 60° C., and wherein the gap between the product bowl and the rotor disc is about 2.5 millimeters and the air velocity through the gap is about 6000 meters per minute, and wherein the binder solution is hydroxypropylmethylcellulose dissolved in water, the hydroxypropylmethylcellulose concentration in the water being about 8 percent by weight, and wherein the binder solution has a temperature of about 40° C. immediately before the binder solution is sprayed, and wherein the binder solution is sprayed at a rate of about 34 grams binder solution per minute per kilogram of riboflavin, the sprayer spray-atomizing the binder solution through a 2-phase binder addition nozzle wherein atomizing air is forced through an outer orifice at a pressure of about 3 bar, and wherein binder is added until the resulting granulate product comprises binder in an amount of from about 3 weight percent to about 5 weight percent, on a dry granulate weight basis.

* * * * *